(12) United States Patent
Zhang et al.

(10) Patent No.: US 8,772,538 B2
(45) Date of Patent: Jul. 8, 2014

(54) PROCESS FOR PRODUCING FORMIC ACID BY HYDROTHERMAL OXIDATION REACTION WITH GLYCEROL AND THEIR EQUIPMENT

(71) Applicant: Tongji University, Shanghai (CN)

(72) Inventors: Yalei Zhang, Shanghai (CN); Zheng Shen, Shanghai (CN); Xuefei Zhou, Shanghai (CN); Min Zhang, Shanghai (CN); Jingfei Zhou, Shanghai (CN)

(73) Assignee: Tongji University, Shanghai (CN)

( * ) Notice: Subject to any disclaimer, the term of this patent is extended or adjusted under 35 U.S.C. 154(b) by 0 days.

(21) Appl. No.: 13/650,245

(22) Filed: Oct. 12, 2012

(65) Prior Publication Data
US 2013/0035507 A1   Feb. 7, 2013

(30) Foreign Application Priority Data
Oct. 17, 2011   (CN) .......................... 2011 1 03128431

(51) Int. Cl.
*C07C 51/00* (2006.01)
(52) U.S. Cl.
USPC .......................................................... 562/538

(58) Field of Classification Search
USPC .......................................................... 562/538
See application file for complete search history.

(56) References Cited

PUBLICATIONS

Zhang, et al. J. Chem. Technol.Biotechnol. 2013, 88, 829-833; Published online in Wiley Online Library: Aug. 28, 2012.*
Pullanikat et al. Tetrahedron Letters 54 (2013) 4463-4466.*
Wolfel et al Green Chem., 2011, 13, 2759.*

* cited by examiner

*Primary Examiner* — Nizal Chandrakumar
(74) *Attorney, Agent, or Firm* — Lowe Hauptman & Ham, LLP (57) ABSTRACT

A process for producing formic acid by hydrothermal oxidation reaction with glycerol and their equipment, wherein glycerol and oxidant are subjected to a hydrothermal oxidation reaction, air, oxygen or $H_2O_2$ as oxidant, at a temperature in the range of 150 to 450° C. and under pressure equal to or more than the saturated vapor pressure at the temperature. The glycerol produced from plant fats, animal fats or the like or pure product synthesized chemically or a discharge containing glycerol generated at the production of diesel fuel oil from fats, in which the fats are subjected to a transesterification with alcohol in the presence of an alkali catalyst in order to obtain fatty acid ester is preferably used as a starting material.

6 Claims, 5 Drawing Sheets

PROCESS FOR PRODUCING FORMIC ACID BY HYDROTHERMAL OXIDATION REACTION WITH GLYCEROL AND THEIR EQUIPMENT

RELATED APPLICATIONS

The present application is based on, and claims priority from, Chinese Application Number 2011103128431, filed Oct. 17, 2011, the disclosure of which is hereby incorporated by reference herein in its entirety.

FIELD OF THE INVENTION

The invention relates to a process for producing formic acid by hydrothermal oxidation reaction with glycerol and their equipment.

BACKGROUND OF THE INVENTION

In recent years, there have been considerable efforts focused on the development of novel technologies for the production of high value-added chemicals from renewable biomass resources in response to the depletion of fossil fuels and worldwide concerns of environmental problems.

Among the various compounds derived from biomass that have been proposed as feedstock for chemical production, glycerol is of special interest because it is produced in large amounts (10 wt %) as a by-product during the production of biodiesel via transesterification. As biodiesel production increases rapidly all over the world, so does the production of primary crude glycerol. Because the global demand for glycerol is limited, the recent increase in glycerol production from the biodiesel manufacturing process has created a glut in the glycerol market.

As a result, crude glycerol is essentially going to waste and has an attached disposal cost. Thus, glycerol has potential to be an important biorefinery feedstock to take advantage of a substance that is both abundant and cheap.

Formic acid is an important chemical feedstock that is mostly used as a synthetic precursor and as a commercial product for use in the leather, agriculture and dye industries. Furthermore, it would be expected that formic acid could be used as a raw material for hydrogen production and that it has the potential to power fuel cells for electricity generation and automobiles.

At present, formic acid is mainly produced from toxic carbon monoxide and water through the carbonylation of NaOH at elevated pressure and temperature. Compared to this traditional method, the process of obtaining formic acid from renewable glycerol is safer, is more sustainable and greener and will be rapidly developed under the present conditions.

Accordingly, formic acid is derived from glycerol, it is gathering an attention in the saving of the petroleum resources and in the reduction of a generation amount of $CO_2$.

SUMMARY OF THE INVENTION

The invention provide a process for producing formic acid by hydrothermal oxidation reaction with glycerol and their equipment. The process inexpensively and is the demand of industrial expected, for glycerol obtained from a wide range including pure products, food waste oil and the like is used.

The process for producing formic acid by hydrothermal oxidation reaction with glycerol, wherein glycerol and oxidant are subjected to hydrothermal oxidation reaction, air, oxygen or $H_2O_2$ as the oxidant.

In the process according to the invention, the glycerol produced from plant fats, animal fats or the like or pure product synthesized chemically is preferably used as a starting material.

In the process according to the invention, as the glycerol, a discharge containing glycerol generated at the production of a diesel fuel oil from fats, in which the fats are subjected to a transesterification with alcohol in the presence of an alkaline catalyst in order to obtain fatty acid ester, is preferably used as a raw material.

In the process according to the invention, the process further comprises a step of performing a gas-liquid separation where formic acid is separated from a gas mixture (including $CO_2$, $CO$, $O_2$ and so on), generated by hydrothermal oxidation reaction.

In the process according to the invention, preferably, the process further comprises a step of concentrating the formic acid in an aqueous solution after the hydrothermal oxidation reaction according to an electrodialysis process.

In the process according to the invention, preferably, the process further comprises a step of separating a liquid of formic acid in an aqueous solution after the hydrothermal oxidation reaction according to a distillation process.

In the process according to the invention, the aqueous solution after the hydrothermal oxidation reaction contains an alkaline owning to biodiesel production process, pH of solution is adjusted with hydrochloric acid or sulfuric acid before the distillation process.

An equipment for producing formic acid of the invention, comprising: a tank for storing raw material 1, a high-pressure pump 2, a pre-heater 3, a reactor 4, a cooler 5, a valve for controlling pressure 7, a tank for storing formic acid 6, wherein all of them are linked through pipes in sequence.

Furthermore, an equipment for producing formic acid of the invention, comprising: a tank for storing raw material 1, a high-pressure pump 2, a heater exchanger 11, a reactor 4, a heater for the heating medium 13, valves for controlling pressure 7,8,9, a gas-liquid separator 12, a neutralization unit; wherein the tank for storing raw material 1, the high-pressure pump 2 and the heater exchanger 11 linked through pipes in sequence; the heater exchanger 11 is connected to the reactor 4 which linked with the heater for the heating medium 13, and the valve for controlling pressure 7 respectively; the valve for controlling pressure 7 is connected to a gas-liquid separator 12 which linked with a valve for controlling pressure 9 and a neutralization unit 10 in sequence, and a valve for controlling pressure 8 respectively.

The equipment for producing formic acid of the invention, preferably, a tank for storing oxidant 14 is connected to the reactor 4. that means the oxidant stored in a tank 14 and supplied to the reactor 4, but not stored in the tank for storing raw material 1 with glycerol.

The equipment for producing formic acid of the invention, alternatively, the value for controlling pressure 9 is connected to a calcium crystallizer 15 but not connected to the neutralization unit 10.

LIST OF REFERENCE NUMBERS

1 tank for storing raw material; 2 high-pressure pump; 3 pre-heater; 4 reactor; 5 cooler; 6 tank for storing formic acid; 7, 8, 9 valves for controlling pressure; 10 neutralization unit; 11 heat exchanger; 12 gas-liquid separator; 13 heater for the heating medium; 14 tank for storing oxidant; 15 calcium crystallizer unit; 20 batch reactor; 21 molten salt bath; 22 heater; 23 agitator; 24 temperature controller; 25 thermocouple.

DETAILED DESCRIPTION OF THE INVENTION

In the following content, methods for utilizing a discharge containing glycerol will be described in detail with reference numbers to the drawings.

Figure 1:
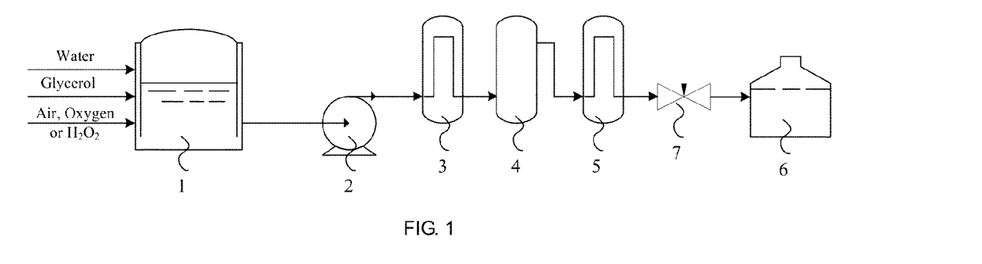
FIG. 1 is a flow sheet for explaining the equipment for producing formic acid of the invention.

FIG. 1 is a flow sheet for explaining the equipment performed using a continuous reactor for producing formic acid according to the invention.

It can be seen from FIG. 1, the equipment for producing formic acid of the invention, comprising: a tank for storing raw material 1, a high-pressure pump 2, a pre-heater 3, a reactor 4, a cooler 5, a valve for controlling pressure 7, a tank for storing formic acid 6, wherein all of them are linked through pipes in sequence.

In the process for producing formic acid of the invention according to FIG. 1, in the beginning, glycerol as a raw material is introduced into a tank for storing raw material 1 together with water and an oxidant such as air, oxygen or $H_2O_2$. The oxidant solution containing glycerol stored in the tank for storing raw material 1 goes through a high-pressure pump 2, a pre-heater 3, a reactor 4 and a cooler 5 sequentially, and, after going through a valve for controlling a pressure 7, finally reaches a tank for storing formic acid solution 6.

The respective configurations are described bellow:

The tank for storing raw material 1 is a tank where the oxidant solution containing a desired amount of glycerol and having desired oxidant supply is prepared by adding appropriate amount of glycerol, oxidant component and water, respectively.

Glycerol added to the tank for storing raw material 1 may be a product derived from decomposition of fats such as plant fats, animal fats or the like or a pure product synthesized chemically. Alternatively, glycerol as a raw material may contain impurities. For instance, as such a glycerol containing impurity, glycerol contained in fats that can be recovered from rendering of fish meats and animal meats, or discharge from plants for a bio-diesel fuel oil, plants for soap and so on can be cited.

A concentration of glycerol is in the range of 1 to 80% by weight and preferably 50% by weight or less from the viewpoint of improving the fluidity owing to lowering of the viscosity.

As the oxidant component, any oxidant substances can be used. Examples thereof include air, oxygen, or $H_2O_2$ and so on. A preferable oxidant supply of an oxidant component is in the range of 100 to 350%.

The high-pressure pump 2 applies predetermined pressure on the oxidant solution containing glycerol from the tank for storing raw material 1 and water is supplied quantitatively.

The pre-heater 3 preliminarily heats the oxidant solution containing glycerol before it is introduced in the reactor 4 where reaction is carried out under a high temperature and high pressure condition. The pre-heater 3 may have a heater for preliminarily heating. Alternatively, the oxidant solution containing glycerol may be heated by a heat exchange at a cooler 5 provided downstream of the reactor 4.

In the reactor 4, the oxidant solution containing glycerol is put under a high temperature and high pressure condition to convert glycerol in the oxidant solution to formic acid. Specifically, the temperature is set in the range of 150 to 450° C. (preferably 200 to 450° C.) and pressure is set at pressure equal to or more than the saturated vapor pressure of water at the above temperature range so that water may retain in a liquid phase.

When reaction is carried out at certain temperature and pressure lower than saturated vapor pressure of water, all water vaporizes and then the reaction is difficult to proceed. Accordingly, the reaction pressure is desirably set to a pressure equal to or more than the saturated vapor pressure at a reaction temperature. The reaction time is largely different depending on the reaction temperature. The higher of the reaction temperature is, or the higher of the oxidant supply, the shorter of the reaction time for converting it into formic acid.

Glycerol in the oxidant solution is converted into formic acid by reaction in the reactor 4. After cooled by the cooler 5, the resultant formic acid solution is transported to a tank for storing formic acid solution 6. The valve for controlling pressure 7 is disposed between the reactor 4 and the tank for storing formic acid solution 6 and the high-pressure state of the formic acid solution is released by the valve 7.

The formic acid solution stored in the tank for storing formic acid solution can be efficiently concentrated using an electrodialysis unit when concentrations of formic acid is low. Furthermore, in the case where formic acid want to be taken out as high concentration from the formic acid solution stored in the tank for storing a formic acid solution 6, formic acid can be taken out as a liquid of formic acid in an aqueous solution by a distillation process.

Figure 2:
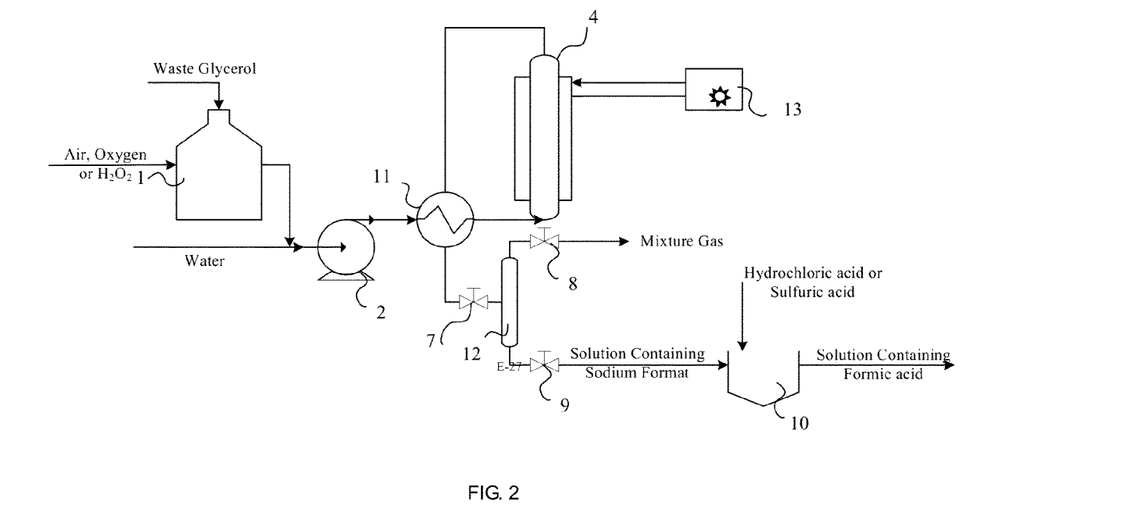
FIG. 2 is another flow sheet for explaining the equipment for producing formic acid of the invention.

FIG. 2 is another flow sheet for explaining the equipment performed using a continuous reactor for producing formic acid according to the invention.

It can be seen from FIG. 2, the equipment for producing formic acid of the invention, comprising: a tank for storing raw material 1, a high-pressure pump 2, a heater exchanger 11, a reactor 4, a heater for the heating medium 13, valves for controlling pressure 7,8,9, a gas-liquid separator 12, a neutralization unit 10. wherein the tank for storing raw material 1, the high-pressure pump 2 and the heater exchanger 11 linked through pipes in sequence; the heater exchanger 11 is connected to the reactor 4 which linked with the heater for the heating medium 13 and the valve for controlling pressure 7 respectively; the valve for controlling pressure 7 is connected to a gas-liquid separator 12 which linked with a valve for controlling pressure 9 and a neutralization unit 10 in sequence, and a valve for controlling pressure 8 respectively.

In the process for producing formic acid and their equipment of the invention according to FIG. 2, in the beginning, a discharge containing glycerol from BDF plants, oleochemical plants and so on is introduced as raw material to a tank for storing raw material 1 together with water and an oxidant such as air, oxygen or $H_2O_2$. The discharge containing glycerol from BDF plants or the like as raw material contains an alkaline component. Furthermore, when an amount of water is scarce, water is appropriately added.

An oxidant solution containing glycerol stored in a tank for storing raw material 1, after water is appropriately added thereto, goes through a high-pressure pump 2, a heat exchanger 11, a reactor 4, a valve for controlling a pressure 7 sequentially and is finally supplied to a gas-liquid separator 12 to separate here the solution into formic acid solution and a mixture gas. The tank for storing raw material 1, the high-pressure pump 2 and the reactor 4, shown in FIG. 2, are the same as those shown in FIG. 1; accordingly detailed explanations thereof are omitted.

In the process for producing formic acid and their equipment of the invention according to FIG. 2, after pressurized to predetermined pressure by the high-pressure pump 2, An oxidant solution containing glycerol stored in the tank for storing raw material is supplied to the heat exchanger 11 to undergo heat-exchange with a gas-liquid mixture fluid (described later) after the hydrothermal oxidation reaction. Thereafter, the oxidant solution containing glycerol heated in the heat exchanger 11 is supplied to the reactor 4.

Glycerol supplied to the reactor is heated by a heating medium (overheated water vapor, silicone oil or the like) transported from a heater for the heating medium 13 in order to be maintained at a predetermined temperature and to undergo a hydrothermal reaction, which leads to a decomposition of glycerol into formic acid.

The fluid composed of a gas-liquid mixture leaves the reactor 4. The fluid is heat-exchanged with the oxidant solution containing glycerol to be supplied to the reactor 4 in order to lower a temperature and is depressurized by the valve for controlling a pressure 7 and then supplied to the gas-liquid separator 12. Since a gas component generated by the hydrothermal oxidation reaction in the reactor 4 is mixture gas, the mixture gas can be removed at the gas-liquid separator 12. In addition, since a liquid component generated by the decomposition of glycerol is certain alkaline solution containing formic acid owning to biodiesel production process, pH of solution is adjusted with hydrochloric acid or sulfuric acid at a neutralization unit 10 before the distillation process. The formic acid solution containing obtained by the above reaction are taken out from the apparatus after adjusting their pressures using valves for controlling a pressure 8 and 9, respectively.

Figure 3:
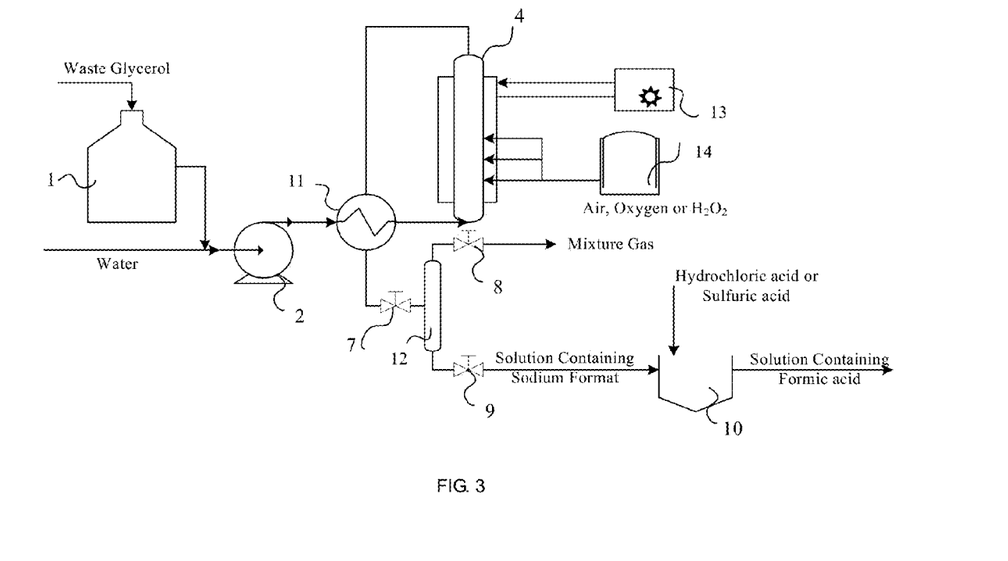
FIG. 3 is another flow sheet for explaining the equipment for producing formic acid of the invention.

FIG. 3 is another flow sheet for explaining the equipment performed using a continuous reactor for producing formic acid according to the invention.

The process for producing formic acid and their equipment of the invention according to FIG. 3 has the same steps and constituents as those in FIG. 2; accordingly, in the description below, the same steps and constituents as those in FIG. 2 are provided with the same steps and reference numbers and detailed explanations are omitted. The difference between FIG. 2 and FIG. 3 is that a tank for storing oxidant 14 is connected to the reactor 4. that means the oxidant stored in a tank 14 and supplied to the reactor 4, but not stored in the tank for storing raw material 1 with glycerol.

In the process for producing formic acid and their equipment of the invention according to FIG. 3, a discharge containing glycerol from BDF plants, oleochemical plants and so on is introduced as a raw material into the tank for storing raw material 1.

An alkaline solution containing glycerol stored in the tank for storing raw material 1, after water is appropriately added thereto, goes through the high-pressure pump 2, the heat exchanger 11, the reactor 4 sequentially. After going through the valve for controlling pressure 7, the solution is finally supplied to the gas-liquid separator 12 to separate the solution into a formic acid solution containing certain alkaline owning to biodiesel production process. The formic acid solution containing certain alkaline obtained by separation in the gas-liquid separator 12 is supplied to a neutralization unit 10 with hydrochloric acid or sulfuric acid in order to remove the alkaline in the solution. The oxidant is supplied to the reactor 4 after storing in a tank for storing oxidant 14.

The process for producing formic acid and their equipment of the invention according to FIG. 3 is different from the process for producing formic acid and their equipment to FIG. 2 in that oxidant is supplied to the reactor 4 instead of the tank for storing raw material 1. This is because the heat exchanger 3 and the high-pressure pump 2 may be inhibited from corrosion due to high concentration of oxidant. As reaction proceeds, oxidant is generated by an oxygen generator or air pump; accordingly, the cost of oxidant supply is lower.

Figure 4:
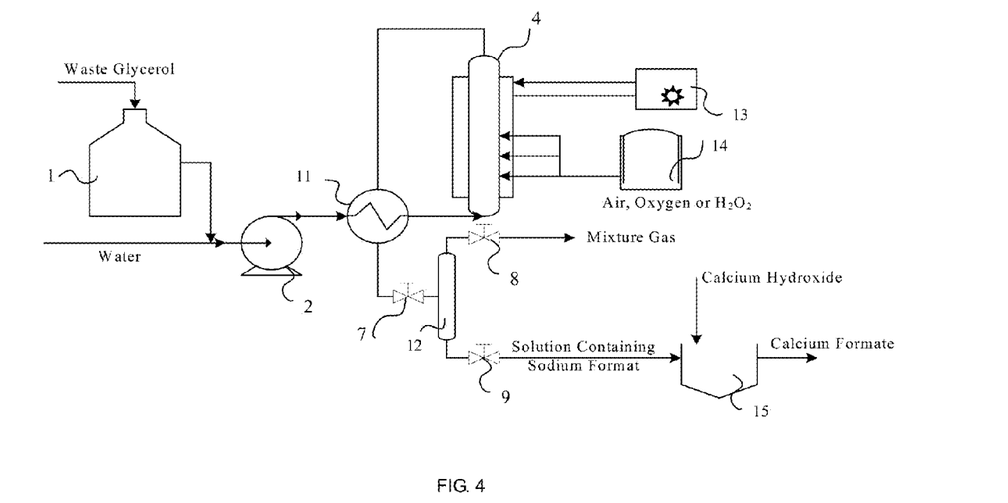
FIG. 4 is another flow sheet for explaining the equipment for producing formic acid of the invention.

FIG. 4 is another flow sheet for explaining the equipment performed using a continuous reactor for producing formic acid according to the invention.

The process for producing formic acid and their equipment of the invention according to FIG. 4 has the same steps and constituents as those of the process for producing formic acid and their equipment according to FIGS. 2 and 3; accordingly, the same steps and constituents are provided with the same steps and reference numbers and the detailed explanations are omitted. The difference between FIG. 3 and FIG. 4 is that the value for controlling pressure 9 is connected to a calcium crystallizer 15 but not connected to the neutralization unit 10.

In the process for producing formic acid and their equipment of the invention according to FIG. 4, after the gas-liquid separation of the solution into formic acid solution containing certain alkaline owning to biodiesel production process in the gas-liquid separator 5, the solution containing sodium formate obtained by the separation is supplied to a calcium crystallizer 15.

The addition of calcium hydroxide in the calcium crystallizer 15 results in a precipitation of salt of calcium formate according to a formula bellow. The precipitated salt is separated from an NaOH solution according to a solid-liquid separation.

According to the invention, following effects can be obtained:

(1) Formic acid can be produced from glycerol discarded from plants for a bio-diesel, oleochemical plants and so on as a raw material (so far, crops have to be cultivated).

(2) In many cases, an alkali used as a catalyst is contained in the glycerol discarded from plants for bio-diesel, oleochemical plants and so on, but such alkali can also be used efficiently in the invention.

(3) A time required for a conversion of glycerol into formic acid is from several minutes to several hours (an existing fermentation process necessarily takes a reaction time of several days).

(4) A conversion rate of formic acid from glycerol is such high as 30% and a reaction by-product is scarce. Accordingly, treatment of waste water is relatively easily applied (in an existing fermentation process, a culture solution for formic acid fermenter has to be treated).

EXAMPLES

Specific examples of the steps described above are set forth in the following examples. However, it will be apparent to one of ordinary skill in the art that many modifications are possible and that the examples are provided for purposes of illustration only and are not limiting of the invention unless so specified.

Example 1

Figure 5:
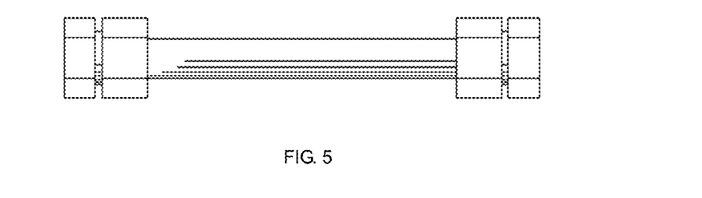
FIG. 5 is a schematic diagram showing a batch reactor used in example 1.

Example 1 is tested in laboratory, a tube made of SUS316 as shown in FIG. 5 and sealed air-tightly with caps was used as a reactor 20. A volume thereof is 5.7 ml, an allowable temperature limit is 450° C. and a withstand pressure is 300 MPa.

An aqueous solution containing 0.45M glycerine and the desired amount of $H_2O_2$ was prepared. The obtained aqueous solution was poured into the reactor 20, followed by air-tightly sealing. A packing ratio of the solution was made not more than 60% by volume of the reactor 20.

Figure 6:
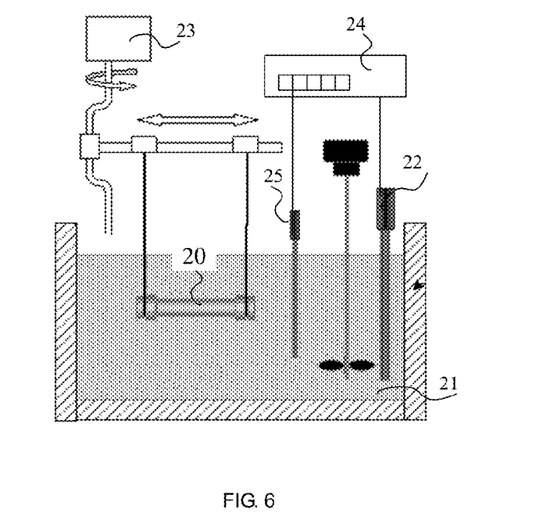
FIG. 6 is a schematic diagram showing a heating shaker used in example 1.

Then, the reactor 20 was immersed in a heating shaker shown in FIG. 6 and shaken for a predetermined time.

A schematic diagram of the heating shaker is shown in FIG. 6. The heating shaker has a molten salt bath 21, a heater 22, an agitator 23, a temperature controller 24 and a thermocouple 25. The heating shaker can be controlled to a temperature in the range of 170 to 450° C. using the temperature controller 24 and the thermocouple 25.

A reaction temperature and a reaction time in the heating shaker were 250° C. and 60 s, respectively. The pressure was made saturated vapor pressure of water at 250° C.

After performing the heating process, the reaction solution was immersed in cold water to rapidly cool.

After performing the cooling, a solution filled in the reactor 20 was taken out, followed by removing a solid component with a 0.45 μm filter, solution was analyzed with high-performance liquid chromatography.

Here, the formic acid yield is defined as the percentage of product to initial glycerine on the basis of carbon.

Figure 7:
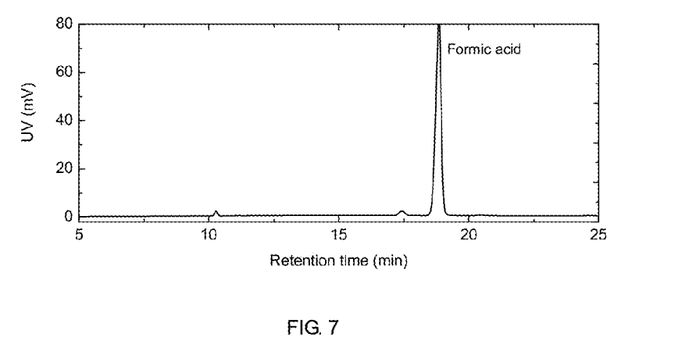
FIG. 7 is a graph of high-performance liquid chromatography analysis showing results of example 1 with an absorbance detector (UV) as a detector.

Analysis results by the high-performance liquid chromatography are shown in FIG. 7 (detector: absorption detector (UV)).

From FIG. 7, it is obvious seen that the main product is formic acid, that means glycerol could be efficiently converted to formic acid.

Example 2

In example 2, to examine the effect of the $H_2O_2$ supply on the yield of formic acid from the oxidation of glycerine, a series of experiments were performed using 0.45M glycerine at 250° C. for 60 s.

Figure 8:
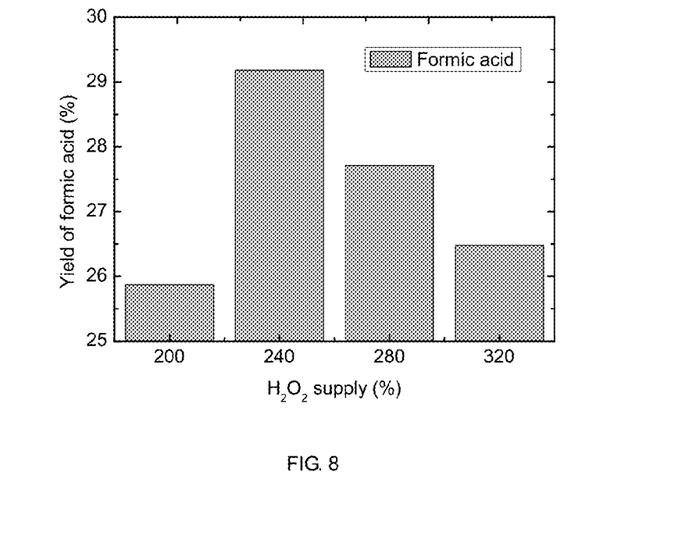
FIG. 8 is a graph showing results of example 2.

Results of example 2 are shown in FIG. 8.

From FIG. 8, it is found that, the yield of formic acid reached a maximum with a 240% $H_2O_2$ supply. The formic acid yield then gradually reduced when further increasing the $H_2O_2$ supply. Adding an excess of $H_2O_2$ resulted in a decrease in the yield of formic acid from a maximum yield of 29.2%. This decrease is likely due to further decomposition of formic acid into $CO_2$ and $H_2O$ with higher $H_2O_2$ supplies.

Example 3

Figure 9:
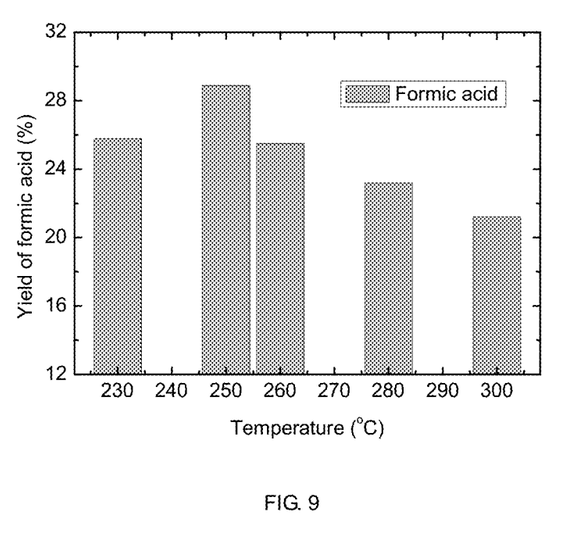
FIG. 9 is a graph showing results of example 3.

In example 3, the effect of the reaction temperature on the production of formic acid was examined for a $H_2O_2$ supply of 240%. The impact of the reaction temperature on the yield of formic acid from the oxidation of glycerine is shown in FIG. 9. As shown in FIG. 9, increasing the reaction temperature from 230° C. to 250° C. resulted in a steady increase in the yield of formic acid from 25.8% to 28.9%. At temperatures greater than 250° C., the formic acid yield gradually decreased with increasing reaction temperature. Therefore, the selection of 250° C. as reaction temperature should be more suitable on the production of formic acid from the oxidation of glycerine.

Example 4

Figure 10:
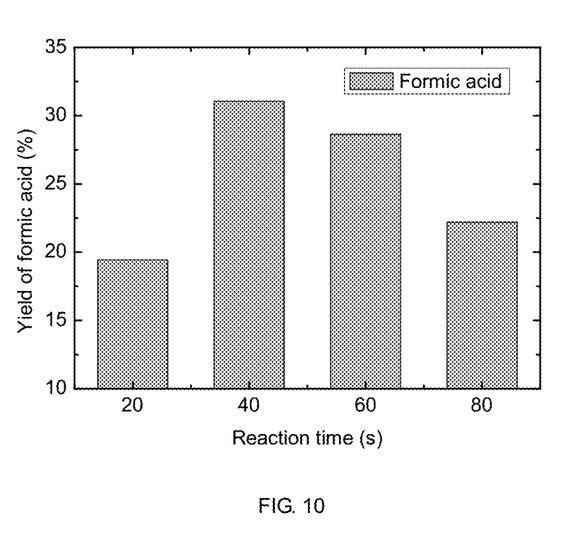
FIG. 10 is a graph showing results of example 4.

In example 4, the effect of the reaction time on the yield of formic acid from the oxidation of glycerine was investigated. As illustrated in FIG. 10, the yield of formic acid gradually increased with increasing reaction time, and the yield reached 31.0% after 40 s. However, the formic acid yield decreased slightly when the reaction time reached 80 s, which suggests that prolonged reaction times resulted in the decomposition of formic acid. This was probably due to further oxidative decomposition of the formed formic acid.

Example 5

Figure 11:
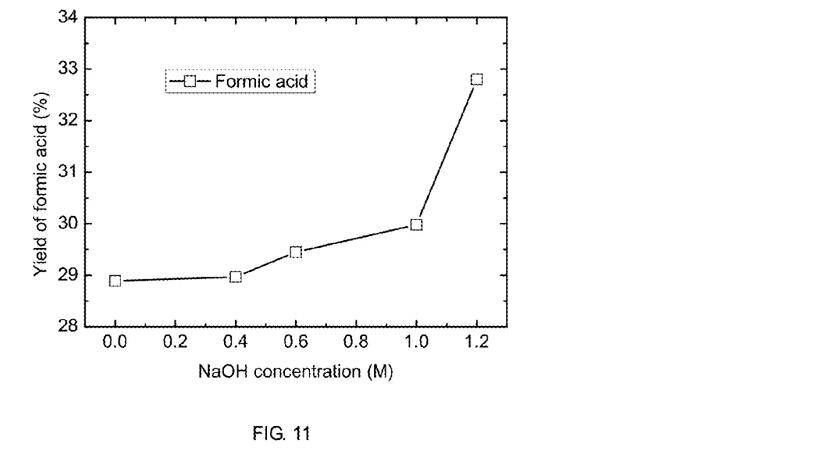
FIG. 11 is a schematic diagram showing a reactor that is used in example 5.

In example 5, effect of the alkali on the production of formic acid from the oxidation of glycerine was investigated. FIG. 11 shows the influence of the addition of an alkali on the yield of formic acid during the oxidation of glycerine. Note that in the above case the real product is formate, rather than formic acid. But, for simplicity, we use the same terminology. From FIG. 11, it can be seen that an increase in alkali concentration resulted in a smooth increase in the yield of formic acid. Even if the alkali concentration is increased to 1.2 M, the formic acid yield merely increased to approximately 32.8% from 28.8%. This result indicated that the addition of an alkali may be not a good way of producing formic acid from the oxidation of glycerine.

Example 6

Figure 12:
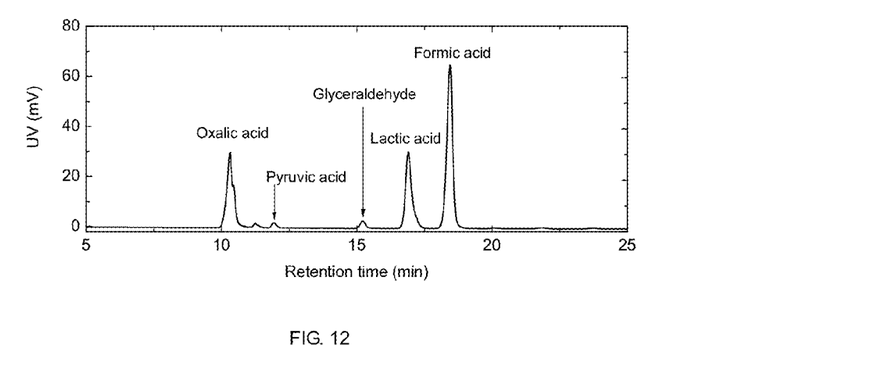
FIG. 12 is a graph showing high-performance liquid chromatography analysis after a reaction of example 6.
Figure 13:
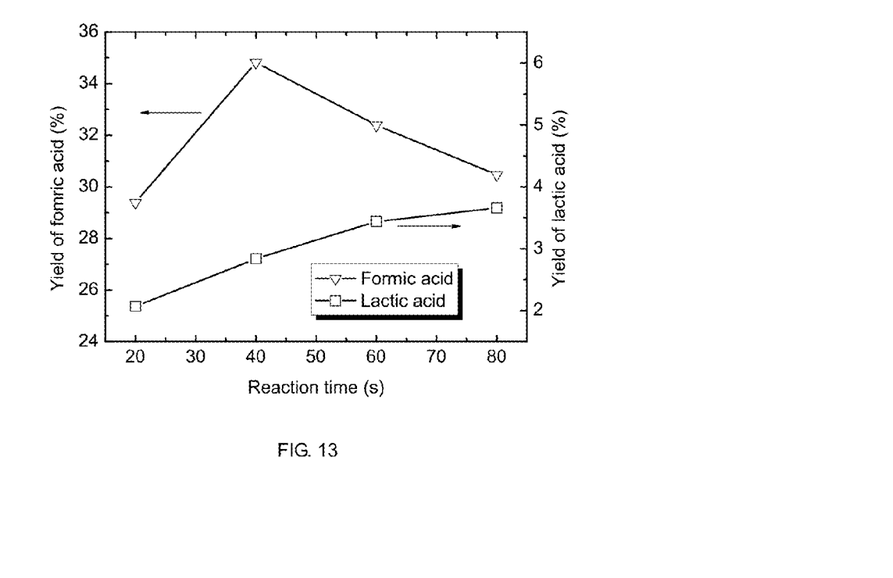
FIG. 13 is a graph showing results of example 6.

In example 6, we investigated the effect of reaction time on the yields of formic acid from the oxidation of glycerine with the addition of 1.2M NaOH. FIG. 12 shows the HPLC chromatogram of the sample solution obtained using 1.2M NaOH for 40 s. An amount of lactic acid was detected in addition to formic and oxalic acids. As shown in FIG. 13, the maximum yield of formic acid was 34.7% and this was obtained with a reaction time of 40 s. The lactic acid yield increased with increasing reaction time, but the yield was only 3.6% at a reaction time of 80 s. This may be because lactic acid was more slowly produced and was more stable than formic acid under these conditions.

Example 7-10

Based on above results of examples 1-6, glycerol and oxidant are subjected to hydrothermal oxidation reaction in a reactor 4 as shown in FIG. 1, or FIG. 2, or FIG. 3, or FIG. 4, wherein air, oxygen or $H_2O_2$ as oxidant, and the oxidant stored in the tank for storing raw material 1 with glycerol or stored in the tank for storing oxidant 14 alone. The temperature of reaction is in the range of 150 to 450° C. (preferably 200 to 450° C.). the other detailed reaction parameters has already described when explaining FIGS. 1 to 4.

The invention claimed is:

1. A process for producing formic acid, wherein glycerol and an oxidant are subjected to a hydrothermal oxidation reaction;
   wherein the oxidant is $H_2O_2$; and
   wherein the hydrothermal oxidation reaction is carried out at a temperature in the range of 150 to 450° C.

2. The process according to claim 1, wherein the hydrothermal oxidation reaction is carried out with the oxidant supply in the range of 50 to 500%, the stoichiometric demand for the complete oxidation of glycerol into formic acid and water was defined as 100% oxidant supply.

3. The process according to claim 1, wherein the glycerol produced from plant fats, animal fats or a pure product synthesized chemically is used as a starting material.

4. The process according to claim 1, wherein the process further comprises a step of performing a gas-liquid separation, wherein formic acid is separated from a gas mixture including $CO_2$, CO, and $O_2$, generated in the hydrothermal oxidation reaction.

5. The process according to claim 1, wherein the process further comprises a step of concentrating the formic acid in an aqueous solution after the hydrothermal oxidation reaction according to an electrodialysis process.

6. The process according to claim 1, wherein the process further comprises a step of separating a liquid of formic acid in an aqueous solution after the hydrothermal oxidation reaction according to a distillation process.

* * * * *